(12) United States Patent
Wingen et al.

(10) Patent No.: US 6,436,489 B1
(45) Date of Patent: Aug. 20, 2002

(54) FLUORINE-CONTAINING BENZOTHIAZOLES, AND THEIR USE IN LIQUID-CRYSTALLINE MIXTURES

(75) Inventors: Rainer Wingen, Hattersheim (DE); Ayako Ogawa, Kakegawa (JP); Barbara Hornung, Hasselroth; Wolfgang Schmidt, Köln, both of (DE)

(73) Assignee: Clariant International Ltd., Muttenz (CH)

( * ) Notice: Subject to any disclaimer, the term of this patent is extended or adjusted under 35 U.S.C. 154(b) by 0 days.

(21) Appl. No.: 09/532,595

(22) Filed: Mar. 22, 2000

(30) Foreign Application Priority Data

Mar. 24, 1999 (DE) .......................... 199 13 312

(51) Int. Cl.$^7$ .................. C09K 19/34; C09K 19/32; C09K 19/30

(52) U.S. Cl. .............. 428/1.1; 252/299.61; 252/299.62; 252/299.63

(58) Field of Search ................. 252/299.61, 299.62, 252/299.63, 299.01; 428/1.1

(56) References Cited

FOREIGN PATENT DOCUMENTS

| | | | |
|---|---|---|---|
| DE | 197 48 432 A | | 5/1999 |
| EP | 0032362 | | 7/1981 |
| EP | 0714893 | | 6/1996 |
| EP | 0733365 | | 9/1996 |
| EP | 0795550 | | 9/1997 |
| JP | 09059266 A | | 3/1997 |
| WO | 95/11890 | * | 5/1995 |

* cited by examiner

*Primary Examiner*—Shean C. Wu
(74) *Attorney, Agent, or Firm*—Frommer Lawrence & Haug LLP

(57) ABSTRACT

Benzothiazoles of the formula (I) are used as components of liquid-crystal mixtures

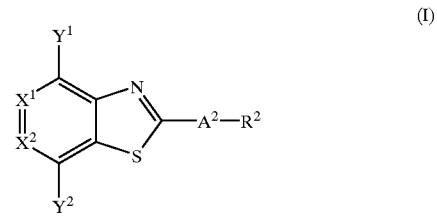

(I)

where the symbols and indices preferably have the following meanings:

$X^1$ and $X^2$, independently of one another, are —CH—, —CF—, the —(R$^1$)—C— group or the —(R$^1$—A$^1$—M$^1$)C— group $Y^1$ and $Y^2$, independently of one another, are hydrogen or fluorine, but are not simultaneously fluorine with the provisos that:

x1) $X^2$ is the —(R$^1$)C— group or the —(R$^1$—A$^1$—M$^1$)C— group, and $X^1$ is —CF—, $Y^1$ is F and $Y^2$ is H, or x2) $X^1$ is the —(R$^1$)C— group or the —(R$^1$—A$^1$—M$^1$)C— group, and $X^2$ is —CF—, $Y^2$ is F and $Y^1$ is H, or x3) $X^2$ is the —(R$^1$)C— group or the —(R$^1$—A$^1$—M$^1$)C— group, and $X^1$ is —CH—, $Y^1$ is H and $Y^2$ is F, or x4) $X^1$ is the —(R$^1$)C— group or the —(R$^1$—A$^1$—M$^1$)C— group, and $X^2$ is —CH—, $Y^2$ is H and $Y^1$ is F $R^1$ and $R^2$, independently of one another, are a straight-chain or branched alkyl radical (with or without asymmetrical carbon atoms) having 1 to 20 carbon atoms, where a) one non-terminal —CH2— group may be replaced by —O—, and/or b) one or more H atoms may be replaced by F, and/or $A^1$ and $A^2$, independently of one another, are phenylene-1,4-diyl, $M^1$ is undirected and is —OC(=O)—, —OC(=O)O—, —OCH$_2$—, —(CH$_2$)$_n$—, —OC(=O)CH$_2$CH$_2$—, —OCH$_2$CH$_2$CH$_2$—, —C≡C— or a single bond n is from 1 to 6.

12 Claims, No Drawings

FLUORINE-CONTAINING BENZOTHIAZOLES, AND THEIR USE IN LIQUID-CRYSTALLINE MIXTURES

Besides nematic and cholesteric liquid crystals, optically active, tilted, smectic (ferroelectric) liquid crystals have also recently been used in commercial display devices.

Clark and Lagerwall have been able to show that the use of ferroelectric liquid crystals (FLCs) in very thin cells results in opto-electrical switching or display elements which have response times which are faster by a factor of up to 1000 compared with conventional TN ("twisted nematic") cells (see, for example, EP-A 0 032 362). Owing to this and other favorable properties, for example the possibility of bistable switching and the fact that the contrast is virtually independent of the viewing angle, FLCs are basically highly suitable for areas of application such as computer displays.

For a more in-depth explanation of the technical requirements of FLCs, see European Patent Application 97118671.3 and DE-A 197 48 432.

Benzothiazole derivatives are disclosed in JP-A 09059266 as components of liquid-crystalline mixtures.

Benzothiazoles having one or more F substituents have been described as constituents of complex structures having a pharmacological action, for example in EP-A-0 714 893,
EP-A-0 795 550, and
EP-A-0 733 365.

These publications do not reveal any suitability of mono- or difluorinated benzothiazoles as components of liquid-crystalline, in particular smectic mixtures and a part of these benzothiazoles.

Since the development, in particular of ferroelectric liquid-crystal mixtures, can in no way be regarded as complete, the manufacturers of displays are interested in a very wide variety of components for mixtures, partly because only the interaction of the liquid-crystalline mixtures with the individual components of the display device or of the cells (for example the alignment layer) allow conclusions to be drawn on the quality of the liquid crystalline mixtures too.

It has now been found that fluorinated benzothiazoles of the formula (I), even when admixed in small amounts, have a favorable effect on the properties of liquid-crystal mixtures, in particular chiral smectic mixtures, for example regarding the dielectric anisotropy and/or the melting point, but also regarding the switching behavior.

The invention relates to the use of compounds of the formula (I) below in liquid-crystal mixtures, preferably smectic and nematic liquid-crystal mixtures, particularly preferably ferroelectric liquid-crystal mixtures. Particular preference is given to use in ferroelectric liquid-crystal mixtures operated in inverse mode or in displays having active matrix elements; very particular preference is given to use in ferroelectric liquid-crystal mixtures operated in inverse mode.

The invention furthermore relates to liquid-crystal mixtures, preferably smectic and nematic liquid-crystal mixtures, particularly preferably ferroelectric liquid-crystal mixtures, which comprise one or more compounds of the formula (I) below

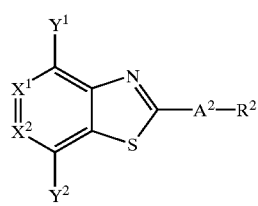

(I)

where the symbols and indices have the following meanings:
$X^1$ and $X^2$, independently of one another, are —CH—, —CF—, the —($R^1$)—C— group or the —($R^1$—$A^1$—$M^1$)C— group
$Y^1$ and $Y^2$, independently of one another, are hydrogen or fluorine, but are not simultaneously fluorine with the provisos that:
x1) $X^2$ is the —($R^1$)C— group or the —($R^1$—$A^1$—$M^1$)C— group, and $X^1$ is —CF—, $Y^1$ is F and $Y^2$ is H, or
x2) $X^1$ is the —($R^1$)C— group or the —($R^1$—$A^1$—$M^1$)C— group, and $X^2$ is —CF—, $Y^2$ is F and $Y^1$ is H, or
x3) $X^2$ is the —($R^1$)C— group or the —($R^1$—$A^1$—$M^1$)C— group, and $X^1$ is —CH—, $Y^1$ is H and $Y^2$ is F, or
x4) $X^1$ is the —($R^1$)C— group or the —($R^1$—$A^1$—$M^1$)C— group, and $X^2$ is —CH—, $Y^2$ is H and $Y^1$ is F,
x5) $X^2$ is the —($R^1$)C— group or the —($R^1$—$A^1$—$M^1$)C— group, and $X^1$ is —CH—, $Y^1$ is F and $Y^2$ is H $R^1$ and $R^2$, independently of one another, are a straight-chain or branched alkyl radical (with or without asymmetrical carbon atoms) having 1 to 20 carbon atoms, where
a) one or two non-terminal —$CH_2$— groups may be replaced by —O— and/or —C(=O)— and/or —Si($CH_3$)$_2$—, with the proviso that two adjacent —$CH_2$— groups cannot be replaced by heteroatoms, and/or
b) one or more —$CH_2$— groups may be replaced by —CH=CH— and/or —C≡C—, and/or
c) one —$CH_2$— group may be replaced by cyclopropane-1,2-diyl, cyclobutane-1,3-diyl, cyclopentane-1,3-diyl, bicyclo-[1.1.1]pentane-1,3-diyl or cyclohexane-1,4-diyl, and/or
d) one or more H atoms may be replaced by F, and/or
e) in the case of a branched alkyl radical containing asymmetrical carbon atoms, the asymmetrical carbon atoms either have —$CH_3$, —$OCH_3$, —$CF_3$, F, CN and/or Cl as substituents, or are incorporated into a 3— to 7-membered ring, in which, in addition, one or two non-adjacent —$CH_2$— groups may be replaced by —O— and one —$CH_2$— group may be replaced by —OC(=O)—

$A^1$ and $A^2$, independently of one another, are phenylene-1,4-diyl, unsubstituted, monosubstituted or disubstituted by CN or F, phenylene-1,3-diyl, unsubstituted, monosubstituted or disubstituted by CN or F, cyclohexane-1,4-diyl, in which one or two H atoms may be replaced by CN and/or $CH_3$ and/or F, 1-cyclohexene-1,4-diyl, in which one H atom may be replaced by F, 1-alkyl-1-silacyclohexane-1,4-diyl, pyridine-2,5-diyl, unsubstituted or monosubstituted by F, pyrimidine-2,5-diyl, unsubstituted or monosubstituted by F, 1,1'-biphenyl-4,4'-diyl, unsubstituted, monosubstituted or disubstituted by F, or 1,1'-phenylcyclohexyl-4,4'-diyl, in which the phenyl moiety is unsubstituted, monosubstituted or disubstituted by F $M^1$ is undirected and is —OC(=O)—, —OC(=O)O—, —$OCH_2$—, —(CH$_2$)$_n$—, —OC(=O)$CH_2CH_2$—, —$OCH_2CH_2CH_2$—, —C≡C— or a single bond n is from 1 to 6.

Undirected is intended to mean that, in the case of asymmetrical groups, mirror and mirror image of the group can be employed.

According to one embodiment, the proviso x5) does not apply.

The symbols and indices in the formula (I) preferably have the following meanings:
$R^1$ and $R^2$, independently of one another, are preferably a straight-chain or branched alkyl radical (with or without asymmetrical carbon atoms) having 2 to 18 carbon atoms, where
a) one —$CH_2$— group may be replaced by —O—, and/or
b) one or more H atoms may be replaced by F.

$R^1$ and $R^2$, independently of one another, are particularly preferably a straight-chain or branched alkyl radical (with or without asymmetrical carbon atoms) having 3 to 16 carbon atoms, where c) one —$CH_2$— group may be replaced by —O—.

$A^1$ and $A^2$, independently of one another, are preferably phenylene-1,4-diyl, phenylene-1,3-diyl, 1,1'-biphenyl-4,4'-diyl or 1,1'-phenylcyclohexyl-4,4'-diyl.

$A^1$ and $A^2$, independently of one another, are particularly preferably phenylene-1,4-diyl.

n may have the value 2, 4, 5 or 6.

The following compounds of the formulae (I-1) to (I-5) are particularly preferably employed:

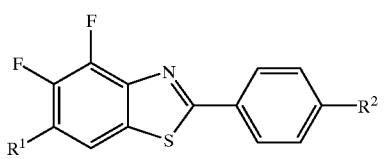
(I-1)

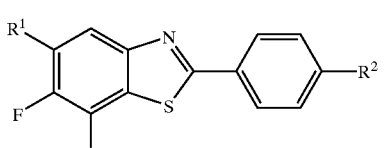
(I-2)

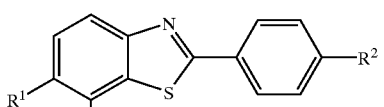
(I-3)

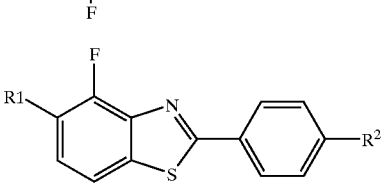
(I-4)

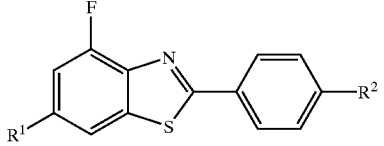
(I-5)

where $R^1$ and $R^2$ have the above-mentioned meanings and preferences.

According to one embodiment of the invention, the formula (I-5) is not one of the preferred compounds.

The invention also relates to the fluorinated benzothiazoles of the formula (1) with the exception of the proviso x4) or the formula (I-4).

The compounds according to the invention and employed according to the invention are prepared by methods known per se from the literature, as described in standard works on organic synthesis, for example Houben-Weyl, Methoden der Organischen Chemie [Methods of Organic Chemistry], Georg-Thieme-Verlag, Stuttgart.

However, it may prove necessary to vary or modify the literature methods for the requirements of mesogenic units, since, for example, functional derivatives having long (>C6) alkyl chains frequently have lower reactivity than, for example, the methyl and ethyl analogs.

Particular reference is made in this connection to the following references, which describe in general terms the synthesis of benzothiazole derivatives, but which do not reveal to the person skilled in the art the fluorinated benzothiazoles according to the invention and their suitability as components of liquid-crystalline mixtures:

Reference 1: Mitsumoto et al., Tokyo Kogyo Koto Senmon Gakko Kenkyu Hokokushu (1993), 25, 73–5 [CAN 121:57382].

Reference 2: Chen et al., Phosphorus, Sulfur Silicon Relat. Elem. (1992), 68(1–4), 205–10 [CAN 117:69775].

As far as the linking of functional derivatives of the fluorinated benzothiazoles with other liquid-crystal-specific units is concerned, express reference is made to DE-A 197 48 432, which gives a list of methods customary to the person skilled in the art.

The liquid-crystal mixtures according to the invention generally comprise from 2 to 35 components, preferably from 2 to 25 components, particularly preferably from 2 to 20 components.

They generally comprise from 0.01 to 80% by weight, preferably from 0.1 to 60% by weight, particularly preferably from 0.1 to 30% by weight, of one or more, preferably from 1 to 10, particularly preferably from 1 to 5, very particularly preferably from 1 to 3, compounds of the formula (I).

Further components of liquid-crystal mixtures which comprise compounds of the formula (I) are preferably selected from known compounds having smectic and/or nematic and/or cholesteric phases. Further mixture components which are suitable in this context are listed, in particular, in international patent application PCT/EP 96/03154 and DE-A 197 48 432, which are expressly incorporated herein by way of reference.

The mixtures according to the invention can in turn be used in electro-optical or fully optical elements, for example display elements, switching elements, light modulators, elements for image processing and/or signal processing, or generally in the area of nonlinear optics.

The invention furthermore relates to a switching or display device, preferably a device utilizing the smectic phases in the region of the working temperature. Particular preference is given to ferroelectric switching and/or display devices operated in normal or inverse ($\tau V_{min}$) mode (see, for example, J. C. Jones, M. J. Towler, J. R. Hughes, Displays 1993, 14, No. 2, 86–93; M. Koden, Ferroelectrics 1996, 179, 121–129).

Particular preference is likewise given to ferroelectric switching and/or display devices containing active matrix elements (see, for example, DE-A 198 22 830).

The present application cites various documents, for example in order to illustrate the technical background to the invention. All these documents are expressly incorporated herein by way of reference.

The invention is explained in greater detail by the examples below without this being intended to represent a restriction thereto.

EXAMPLE 1

4,5-Difluoro-6-hexyl-2-(4-hexylphenyl) benzothiazole

2-Amino-3,4-difluorothiophenol [131105–92–5] is reacted analogously to Reference 1 with 4-hexylbenzaldehyde (commercially available, [49763-69-1]) to give 4,5-difluoro-2-(4-hexylphenyl)benzothiazoline, which is converted into 4,5-difluoro-2-(4-hexylphenyl) benzothiazole using barium permanganate by the method described in the cited literature. a-Lithiation (by means of lithium diisopropylamide analogously to J. Chem. Soc. Perkin Trans. II 1989, 2048) and quenching with hexyl bromide gives the target compound, which can be purified by chromatography and by recrystallization from acetonitrile.

The compounds of the formula (I) in which

R$^1$ (in the R$^1$—C group) is an alkyl radical having 1 to 20 carbon atoms, in which, in addition, one —CH$_2$— group (not adjacent to the ring) may be replaced by —O— or one —CH$_2$— group may be replaced by —Si(CH$_3$)$_2$—, —CH=CH—, —C≡C— or cyclohexane-1,4-diyl, and R$^2$ can be an alkyl or alkoxy radical having 1 to 20 carbon atoms, in which, in addition, one —CH$_2$— group may be replaced by —Si(CH$_3$)$_2$—, —CH=CH—, —C≡C— or cyclohexane-1,4-diyl can be obtained analogously.

EXAMPLE 2

4,5-Difluoro-6-hexyloxy-2-(4-hexylphenyl)benzothiazole is obtained analogously to Example 1, but, after lithiation, is converted into the corresponding boronic acid using trimethyl borate and this product is in turn converted into 4,5-difluoro-6-hydroxy-2-(4-hexylphenyl)benzothiazole using hydrogen peroxide. The target compound is obtainable from this product by means of hexan-1-ol under the conditions of a Mitsunobu reaction.

The compounds of the formula (I) in which

R$^1$ (in the —(R$^1$)C— group) is an alkoxy radical having 1 to 20 carbon atoms, in which, in addition, the —CH$_2$— group adjacent to the oxygen may be replaced by —C(=O)— and/or one —CH$_2$— group may be replaced by —Si(CH$_3$)$_2$—, —CH=CH—, —C≡C— or cyclohexane-1,4-diyl, or R$^1$ (in the —(R$^1$—A$^1$—M$^1$)C— group) is an alkyl or alkoxy radical having 1 to 20 carbon atoms, in which, in addition, one —CH$_2$— group may be replaced by —Si(CH$_3$)$_2$—, —CH=CH—, —C≡C— or cyclohexane-1,4-diyl, and in each case R$^2$ can be an alkyl or alkoxy radical having 1 to 20 carbon atoms, in which, in addition, one —CH$_2$— group may be replaced by —Si(CH$_3$)$_2$—, —CH=CH—, —C≡C— or cyclohexane-1,4-diyl can be obtained analogously.

EXAMPLE 3

6,7-Difluoro-5-hexyl-2-(4-hexylphenyl)benzothiazole is obtained analogously to Example 1, but using 2-amino-5,6-difluorothiophenol [143163-90-0].

The compounds of the formula (I) in which a) R$^1$ (in the —(R$^1$)C— group) is an alkyl radical having 1 to 20 carbon atoms, in which, in addition, one —CH$_2$— group (not adjacent to the ring) may be replaced by —O— or one —CH$_2$— group may be replaced by —Si(CH$_3$)$_2$—, —CH=CH—, —C≡C— or cyclohexane-1,4-diyl, and R$^2$ can be an alkyl or alkoxy radical having 1 to 20 carbon atoms, in which, in addition, one —CH$_2$— group may be replaced by —Si(CH$_3$)$_2$—, —CH=CH—, —C≡C— or cyclohexane-1,4-diyl or b) R$^1$ (in the —(R$^1$)C— group) is an alkoxy radical having 1 to 20 carbon atoms, in which, in addition, the —CH$_2$— group adjacent to the oxygen may be replaced by —C(=O)— and/or one —CH$_2$— group may be replaced by —Si(CH$_3$)$_2$—, —CH=CH—, —C≡C— or cyclohexane-1,4-diyl, or R$^1$ (in the —(R$^1$—A$^1$—M$^1$)C— group) is an alkyl or alkoxy radical having 1 to 20 carbon atoms, in which, in addition, one —CH$_2$— group may be replaced by —Si(CH$_3$)$_2$—, —CH=CH—, —C≡C— or cyclohexane-1,4-diyl, and in each case R$^2$ can be an alkyl or alkoxy radical having 1 to 20 carbon atoms, in which, in addition, one —CH$_2$— group may be replaced by —Si(CH$_3$)$_2$—, —CH=CH—, —C≡C— or cyclohexane-1,4-diyl can be obtained analogously.

EXAMPLE 4

6-Methyl-7-fluoro-2-(4-hexylphenyl)benzothiazole

The reaction procedure analogous to Example 1, but using 2-amino-6-fluoro-5-methylthiophenol [131105-94-7], gives 6-methyl-7-fluoro-2-(4-hexylphenyl)benzo-thiazoline. The target structure is obtained by dehydrogenation by means of dichlorodicyanobenzoquinone (DDQ) analogously to Reference 2, purification by chromatography and recrystallization from acetonitrile.

By using alkyl-homologous thiophenols or by functionalization of the methyl group (for example by bromination by means of NBS to give the bromomethyl compound, which can then undergo metal-catalyzed C—C coupling reactions, for example using alkylmagnesium halides), analogous compounds of the formula (I) in which R$^1$ (in the —(R$^1$)C— group) is an alkyl radical having 1 to 20 carbon atoms, in which, in addition, one —CH$_2$— group (not adjacent to the ring) may be replaced by —O— or one —CH$_2$— group may be replaced by —Si(CH$_3$)$_2$—, —CH=CH—, —C≡C—or cyclohexane-1,4-diyl can be obtained.

What is claimed is:

1. A liquid-crystalline mixture comprising at least one benzothiazole of the formula (I)

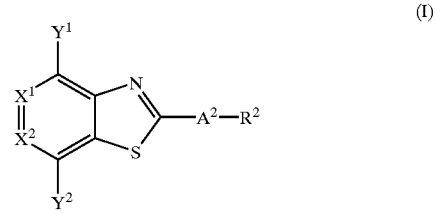

where the symbols and indices have the following meanings:

X$^1$ and X$^2$, independently of one another, are —CH—, —CF—, the —(R$^1$)—C— group or the —(R$^1$—A$^1$—M$^1$)C— group Y$^1$ and Y$^2$, independently of one another, are hydrogen or fluorine, but are not simultaneously fluorine with the provisos that:

x1) X$^2$ is the —(R$^1$)C— group or the —(R$^1$—A$^1$—M$^1$)C— group, and X$^1$ is —CF—, Y$^1$ is F and Y$^2$ is H, or x2) X$^1$ is the —(R$^1$)C— group or the —(R$^1$—A$^1$—M$^1$)C— group, and X$^2$ is —CF—, Y$^2$ is F and Y$^1$ is H, or x3) X$^2$ is the —(R$^1$)C— group or the —(R$^1$—A$^1$—M$^1$)C— group, and X$^1$ is —CH—, Y$^1$ is H and Y$^2$ is F, or x4) $X^1$ is the —($R^1$)C— group or the —($R^1$—$A^1$—$M^1$)C— group, and $X^2$ is —CH—, $Y^2$ is H and $Y^1$ is F, x5) $X^2$ is the —($R^1$)C— group or the —($R^1$—$A^1$—$M^1$)C— group, and $X^1$ is —CH—, $Y^1$ is F and $Y^2$ is H $R^1$ and $R^2$, independently of one another, are a straight-chain or branched alkyl radical (with or without asymmetrical carbon atoms) having 1 to 20 carbon atoms, where a) one or two non-terminal —$CH_2$— groups may be replaced by —O— and/or —C(=O)— and/or —Si($CH_3$)$_2$—, with the proviso that two adjacent —$CH_2$— groups cannot be replaced by heteroatoms, and/or b) one or more —$CH_2$— groups may be replaced by —CH=CH— and/or —C≡C—, and/or c) one —$CH_2$— group may be replaced by cyclopropane-1,2-diyl, cyclobutane-1,3-diyl, cyclopentane-1,3-diyl, bi-cyclo[1.1.1]pentane-1,3-diyl or cyclohexane-1,4-diyl, and/or d) one or more H atoms may be replaced by F, and/or e) in the case of a branched alkyl radical containing asymmetrical carbon atoms, the asymmetrical carbon atoms either have —$CH_3$, —$OCH_3$, —$CF_3$, F, CN and/or Cl as substituents, or are incorporated into a 3- to 7-membered ring, in which, in addition, one or two non-adjacent —$CH_2$— groups may be replaced by —O— and one —$CH_2$— group may be replaced by —OC(=O)—

$A^1$ and $A^2$, independently of one another, are phenylene-1,4-diyl, unsubstituted, monosubstituted or disubstituted by CN or F, phenylene-1,3-diyl, unsubstituted, monosubstituted or disubstituted by CN or F, cyclohexane-1,4-diyl, in which one or two H atoms may be replaced by CN and/or $CH_3$ and/or F, 1-cyclohexene-1,4-diyl, in which one H atom may be replaced by F, 1-alkyl-1-silacyclohexane-1,4-diyl, pyridine-2,5-diyl, unsubstituted or monosubstituted by F, pyrimidine-2,5-diyl, unsubstituted or monosubstituted by F, 1,1'-biphenyl-4,4'-diyl, unsubstituted, monosubstituted or disubstituted by F, or 1,1'-phenylcyclohexyl-4,4'-diyl, in which the phenyl moiety is unsubstituted, monosubstituted or disubstituted by F $M^1$ is undirected and is —OC(=O)—, —OC(=O)O—, —$OCH_2$—, $(CH_2)_n$—, —OC(=O)$CH_2CH_2$—, —$OCH_2CH_2CH_2$—, —C≡C— or a single bond n is from 1 to 6.

2. A liquid-crystalline mixture as claimed in claim 1, in which $R^1$ and $R^2$, independently of one another, are straight-chain or branched alkyl radicals (with or without asymmetrical carbon atoms) having 2 to 18 carbon atoms, where a) one —$CH_2$— group may be replaced by —O—, and/or b) one or more H atoms may be replaced by F.

3. A liquid-crystalline mixture as claimed in claim 1, in which $R^1$ and $R^2$, independently of one another, are straight-chain or branched alkyl radicals (with or without asymmetrical carbon atoms) having 3 to 16 carbon atoms, where a) one —$CH_2$-group may be replaced by —O—.

4. A liquid-crystal mixture as claimed in claim 1, in which $A^1$ and $A^2$, independently of one another, are phenylene-1,4-diyl, phenylene-1,3-diyl, 1,1'-biphenyl4,4'-diyl or 1,1'-phenylcyclohexyl-4,4'-diyl.

5. A liquid-crystal mixture as claimed in claim 4, in which $A^1$ and $A^2$ are phenylene-1,4-diyl.

6. A liquid-crystal mixture as claimed in claim 1, which comprises from 0.01 to 80% by weight of one or more compounds of the formula (I).

7. A liquid-crystal mixture as claimed in claim 1, which is ferroelectric (chiral smectic).

8. A liquid-crystal mixture as claimed in claim 1, which is nematic.

9. A ferroelectric switching and/or display device containing a ferroelectric liquid-crystal mixture as claimed in claim 1.

10. A ferroelectric switching and/or display device as claimed in claim 9, which is operated in $\tau V_{(min)}$ mode.

11. A ferroelectric switching and/or display device as claimed in claim 9, which contains active matrix elements.

12. The liquid-crystal mixture as defined in claim 1 wherein said at least one benzothiazole is of the formula (I) with the exception of the compounds of the proviso x4).

* * * * *